United States Patent [19]

Ozawa et al.

[11] Patent Number: 4,504,483
[45] Date of Patent: Mar. 12, 1985

[54] FLUORINE SUBSTITUTED PYRIDINE METHYL ESTERS AND INSECTICIDAL AND ACARICIDAL COMPOSITIONS THEREOF

[75] Inventors: Kiyomi Ozawa; Masataka Hatanaka, both of Funabashi; Masayoshi Hirose; Masaki Kudo, both of Shiraoka, all of Japan

[73] Assignee: Nissan Chemical Industries Ltd., Tokyo, Japan

[21] Appl. No.: 408,912

[22] Filed: Aug. 17, 1982

[30] Foreign Application Priority Data

Aug. 25, 1981 [JP]  Japan ................................ 56-132856

[51] Int. Cl.³ .......................................... C07D 213/64
[52] U.S. Cl. .................................. 514/351; 546/300; 568/579; 549/434
[58] Field of Search ........................ 546/300; 424/263

[56] References Cited

U.S. PATENT DOCUMENTS

| | | | |
|---|---|---|---|
| 4,163,787 | 8/1979 | Malhotra et al. | 546/300 |
| 4,258,048 | 3/1981 | Heertum et al. | 546/300 |
| 4,262,001 | 4/1981 | Malhotra et al. | 546/300 |
| 4,264,606 | 4/1981 | Ozawa et al. | 546/300 |
| 4,315,012 | 2/1982 | Martel et al. | 546/300 |
| 4,322,534 | 3/1982 | Baum | 546/300 |
| 4,357,335 | 11/1982 | Martel | 546/300 |

OTHER PUBLICATIONS

Derwent Abst. 74411C/42, 27348E/14, 42893E/21, 29869E/15.

Primary Examiner—Jane T. Fan

Attorney, Agent, or Firm—Oblon, Fisher, Spivak, McClelland & Maier

[57]  ABSTRACT

Fluorine substituted pyridine methyl esters having the formula

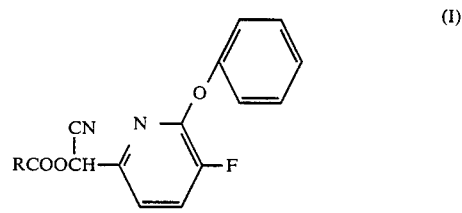

wherein R represents

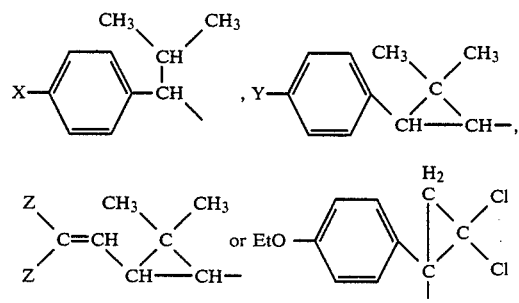

in which X is chlorine or difluoromethoxy; Y is chlorine or tert-butyl; and Z is a halogen atom, are novel compounds which are useful as insecticides and acaricides.

11 Claims, No Drawings

FLUORINE SUBSTITUTED PYRIDINE METHYL ESTERS AND INSECTICIDAL AND ACARICIDAL COMPOSITIONS THEREOF

BACKGROUND OF THE INVENTION

1. Field of the Invention

The present invention relates to compounds which have excellent insecticidal and acaricidal activities to various insect pests in sanitation as well as agriculture, horticulture and forest.

2. Description of the Prior Art

Recently, structure modifications of natural pyrethrin have been widely studied and various pyrethroids have been developed and used as insecticides. Even today, there is a demand for development of new chemicals having more excellent insecticidal and acaricidal characteristics.

The inventors have studied the syntheses and biochemical activities of various compounds in the development of compounds having insecticidal and acaricidal activities which are superior to the known compounds.

Heretofore, it has been known that certain cyano(6-phenoxy-2-pyridyl) methyl esters of carboxylic acids such as 2,2-dimethyl-3-dichlorovinyl-cyclopropane carboxylic acid (Japanese Unexamined Patent Publication No. 112881/1978) or α-isopropyl-p-chlorophenyl acetic acid (Japanese Unexamined Patent Publication No. 115869/1980 or U.S. Pat. No. 4,228,172) have an insecticidal activity.

SUMMARY OF THE INVENTION

It is an object of the present invention to provide insecticidal and acaricidal compounds which have high insecticidal and acaricidal effects and low toxicity to mammals and fishes.

Briefly, the foregoing and other objects of the present invention have been attained by providing insecticidal and acaricidal compounds of fluorine substituted pyridine methyl esters having the formula

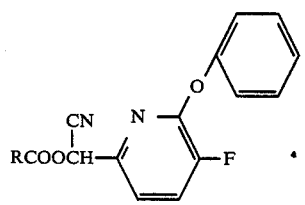

(I)

wherein R represents

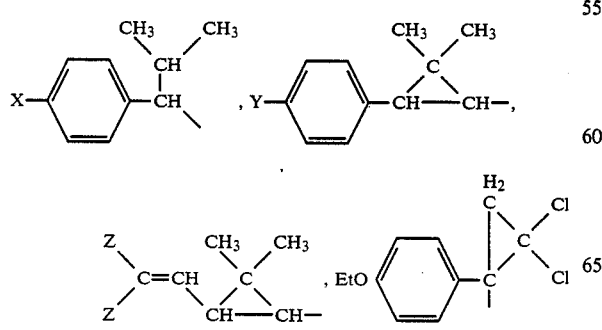

in which X is chlorine or difluoromethoxy; Y is chlorine or tert-butyl; and Z is a halogen atom.

DETAILED DESCRIPTION OF THE PREFERRED EMBODIMENTS

The novel compounds of fluorine substituted pyridine methyl esters having the formula (I) have excellent insecticidal and acaricidal effect. As described in the following examples the insecticidal and acaricidal activity of the compounds of the present invention is significantly superior to that of the known compounds which have a similar structure.

It is an unexpected result from the conventional knowledge that the compounds of the present invention have excellent insecticidal and acaricidal activity.

The process for producing these compounds will be illustrated by the following schemes (A) to (D).

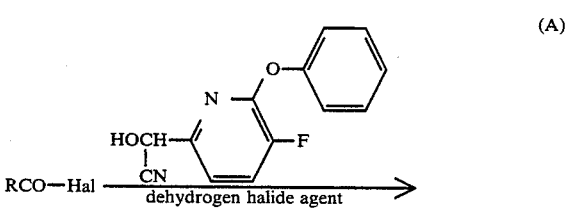

(A)

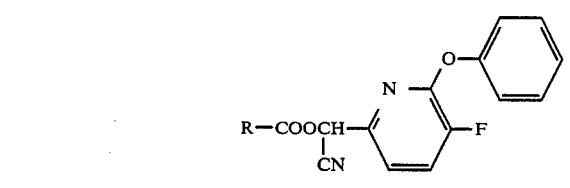

(B)

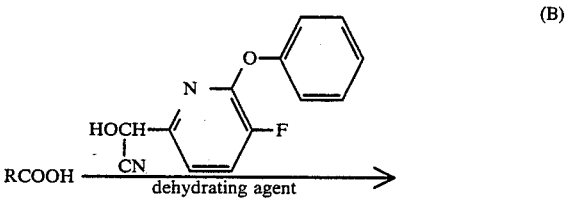

(C)

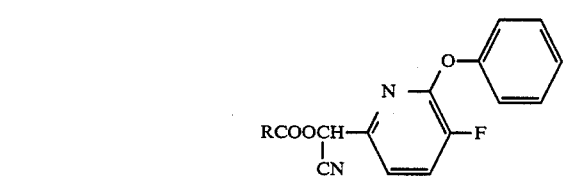

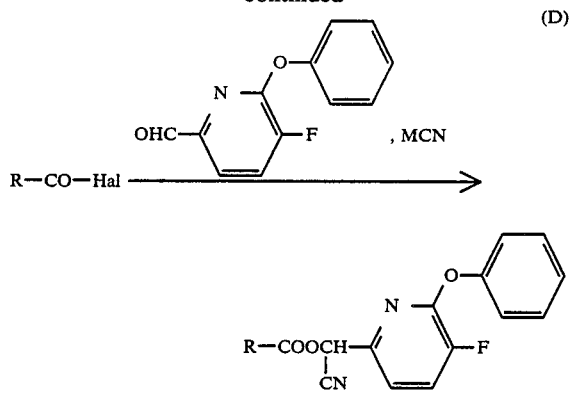

In the schemes (A) to (D), R is as defined above and Hal represents a halogen atom and W represents a halogen atom or a sulfonate group and M represents sodium or potassium.

The processes are further illustrated in detail as follows.

In the process (A), an organic tertiary base such as pyridine and triethylamine or an inorganic base such as alkali metal or alkaline earth metal hydroxides is used as the dihydrogen halide agent and the starting materials are reacted in an inert solvent such as benzene.

In the process (B), the starting components are reacted in an inert solvent such as acetonitrile in the presence of a dehydrating agent such as dicyclohexylcarbodiimide. Alternatively, p-toluenesulfonic acid or conc. sulfuric acid used in an esterification can be used as the catalyst.

In the process (C), the starting materials are reacted in a solvent such as dimethylformamide, preferably under refluxing. In the course of the reaction, an alkali metal or alkaline earth metal hydroxide is used for converting an acid to a salt such as potassium or sodium salt etc.

In the process (D), the starting materials are reacted in an aprotic solvent which is not miscible to water such as n-heptane in the presence of water soluble cyan compound such as sodium cyanate and a phase transfer catalyst such as tetra-n-butyl ammonium chloride or trimethyl benzylammonium chloride to obtain the compound of the present invention in high yield.

The starting materials, cyano(5-fluoro-6-phenoxy-2-pyridyl) methyl alcohol and 5-fluoro-6-phenoxy picolinic aldehyde, used in the schemes (A) to (D), are novel compounds which can be prepared according to the following reaction scheme (E).

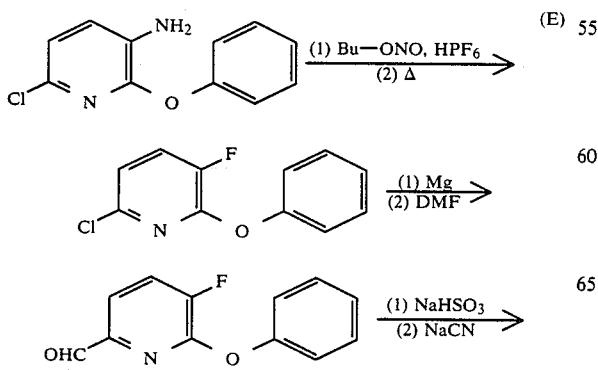

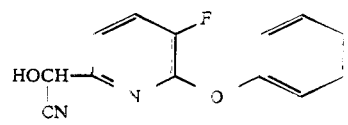

A diazonium salt is formed by reacting 2-chloro-5-amino-6-phenoxypyridine with butyl nitrite in the presence of HPF$_6$ and is decomposed by heating (Baltz-Schiemann reaction) to obtain 2-chloro-5-fluoro-6-phenoxypyridine. The obtained product is reacted with magnesium and then with a formylating agent such as dimethylformamide to obtain 5-fluoro-6-phenoxy picolinic aldehyde. In the case where cyano(5-fluoro-6-phenoxy-2-pyridyl) methyl alcohol is required, it is prepared by reacting the aldehyde with sodiumbisulfite and then with a cyanide compound such as sodium cyanide.

The typical esters of the present invention are given in Table 1.

TABLE 1

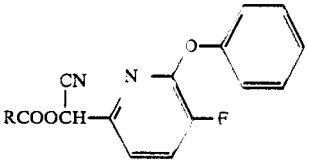

| Compound No. | R | Refractive index ($n_D^{20}$) |
|---|---|---|
| 1 | 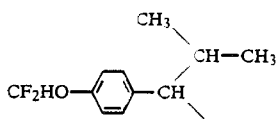 | .5464 |
| 2 | 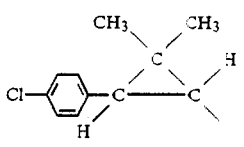 | .5329 |
| 3 | 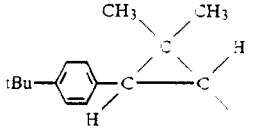 | .5648 |
| 4 | 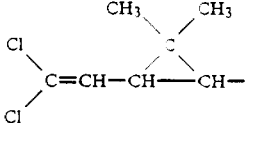 | .5430 |
| 5 | 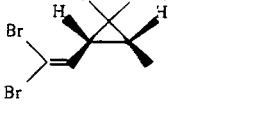 | .5600 |
| 6 | Br, Br, CH$_3$, CH$_3$, H, H | .5816 |

TABLE 1-continued (I)

[Structure: pyridine ring with O-phenyl, F substituent, and RCOOCH(CN)- group]

| Compound No. | R | Refractive index ($n_D^{20}$) |
|---|---|---|
| 7 | [Structure: EtO-phenyl-C(CH2Cl)(C)(Cl) cyclopropane] | 1.5660 |

The serial numbers of the compounds given in Table 1 are referred in the following examples of Preparations, Compositions and Tests.

The esters of the present invention, of course, include optical isomers thereof due to the asymmetric carbon atom at the carboxylic acid moiety and at the alcohol moiety, and geometrical isomers thereof due to the stereochemical structure in some carboxylic acid moieties.

The compounds of the present invention are useful as insecticides for controlling insect pests in sanitation, and various insect pests in agriculture and horticulture which cause damages to rice, vegetable, fruits, cotton, and other crop plants and flowers and insect pests in forest and insect pests in storages.

The typical insect pests which are controlled by the compounds of the present invention are provided for purposes of illustration only.

Orthoptera
| | |
|---|---|
| German Cockroach | (Blattella germanica) |
| Rice Grasshopper | (Oxya yezoensis) |

Thysanoptera
| | |
|---|---|
| Rice Thrips | (Baliothrips biformis) |

Hemiptera
| | |
|---|---|
| Rice Stink Bug | (Lagynotomus elongatus) |
| Green Stink Bug | (Nezcra antennata) |
| Rice Bug | (Leptocorisa chinensis) |
| Bean Bug | (Riotortus clavatus) |
| Cotton Bug | (Dysdercus cingulatus) |
| Grape Leafhopper | (Epiacanthus stramineus) |
| Green Rice Leafhopper | (Nephotettix cincticeps) |
| Small Brown Planthopper | (Laodelphax striatellus) |
| Brown Rice Planthopper | (Nilaparvata lugens) |
| White-backed Rice Planthopper | (Sogatella furcifera) |
| Citrus Psylla | (Diaphorina citri) |
| Greenhouse Whitefly | (Trialeurodes vaporariorum) |
| Cowpea Aphid | (Aphis craccivora) |
| Cotton Aphid | (Aphis gossypii) |
| Apple Aphid | (Aphis spiraecola) |
| Green Peach Aphid | (Myzue persicae) |
| Citrus Mealybug | (Planococcus citri) |
| Comstock Mealybug | (Pseudcoccus censtocki) |
| Red Scale | (Aonidiella aurantri) |
| San Jose Scale | (Comstockaspis perniciosa) |
| Arrowhead Scale | (Unaspis yanonensis) |

Lepidoptera
| | |
|---|---|
| Apple Leafminer | ((Phyllonorycfer ringoneella) |
| Citrus Leafminer | (Phyllocnistis citrella) |
| Diamondback Moth | (Plutella xylostella) |
| Pink Bollworm | (Pectinophora gossypiella) |
| Potato Tuberworm | (Phthorimaea operculella) |
| Peach Fruit Moth | (Carposina niponensis) |
| Summer Fruit Tortrix | (Adoxophyes orana) |
| Oriental Fruit Moth | (Grapholita molesta) |
| Soybean Pod Borer | (Leguminivora glycinivorella) |
| Rice Stem Borer | (Chila suppressalis) |
| Rice Leafroller | (Chaphalocrocis medinalis) |
| Pea Pod Borer | (Etiella zinckenella) |
| Oriental Corn Borer | (Ostrinia furnacalis) |
| Yellow Rice Borer | (Tryporyza incertulas) |
| Cutworm | (Agrotis segetum) |
| Cotton Looper | (Anomis flava) |
| American Bollworm, Cotton Bollworm or Tabacco Budworm | (Heliothis armigera, H. zea H. virescens) |
| Cabbage armyworm | (Mamestra brassicae) |
| Beet Semi Looper | (Plusia nigrisigna) |
| Rice Armyworm | (Pseudaletia separata) |
| Pink Borer | (Sesamia inferens) |
| Common Cutworm | (Spodoptcra litura) |
| Common White | (Pieris rapae crucivora) |
| Smaller Citrus Dog | (Papilio xuthus) |
| Rice Skipper | (Parnara guttata) |
| Codling Moth | (Cydia pomonella) |

Coleoptera
| | |
|---|---|
| Cupreous Chafer | (Anomala cuprea) |
| Asiatic Garden Beetle | (Maladera castanea) |
| Japanese Beetle | (Popillia Japonica) |
| Twenty-eight-spotted Lady beetle | (Henosepilachna vigintioctopunctata) |
| Cucurbit Leaf Beetle | (Aulacophora femoralis) |
| Rice Leaf Beetle | (Oulema oryzae) |
| Striped Flea Beetle | (Phyllotreta striolata) |
| Rice Plant Weevil | (Echinocnemus squameus) |
| Rice Water Weevil | (Lissorhoptrus oryzophilus) |
| Vegetable Weevil | (Listroderes obliquus) |
| Maize Weevil | (Sitophilus zeamais) |
| Bull Weevil | (Anthonomus grandis) |
| Corn Rootworms | ( Diabrotic spp.) |
| Colorado Potato Beetle | (Leptinotarsa decemlineata) |

Hymenoptera
| | |
|---|---|
| Fire Ant | (Solenopsis geminata) |

Diptera
| | |
|---|---|
| Soybean Pud Gall Midge | ( Asphondylia spp.) |
| Oriental Fruit Fly | (Dacus dorsalis) |
| Rice Leafminer | (Hydrellia griseola) |
| Rice Stem Maggot | (Chlorops oryzae) |
| Rice Leafminer | (Agromyza oryzae) |
| Seedcorn Maggot | (Hylemya platura) |
| Mediterranean Fruit Fly | (Ceratitis capitata) |
| Rice Gall Midge | (Orseolia oryzae) |
| House Fly | (Musca domestica) |
| Pale House Mosquito | (Culex pipiens pallens) |

Isoptera
| | |
|---|---|
| Termites | (Coptotermes formosanus) |

The insecticidal activity of the compounds of the present invention is imparted not only two young larva but also to old larva directly or in penetration by direct contact or immersion. The compounds of the present invention are also effective to control various acarinas and nematodes.

In the application of the insecticidal composition of the present invention, it is preferable to apply it at a concentration of 0.01 to 10,000 ppm preferably 0.1 to 2,000 ppm of the active ingredient. In order to control aquatic insect pests, the composition having said concentration can be sprayed to the part to control the aquatic insect pests. Therefore, the concentration of the active ingredient in water can be lower.

In the application of the compound of the present invention as the insecticide, it is preferable to prepare a composition by mixing the active ingredient with a desired solid carrier such as clay, talc and bentonite; or a liquid carrier such as water, alcohols (methanol, ethanol etc.), ketones, ethers, aliphatic hydrocarbons, aromatic hydrocarbons (benzene, toluene, xylene etc.), esters and nitriles, if necessary, with an emulsifier, a dispersing agent, a suspending agent, a spreader, a penetrant and a stabilizer so as to form suitable compositions for practical applications in the form of an emulsifiable concentrate, an oil spray, a wettable powder, a dust, a granule, a tablet, a paste, a flowable, a bait poison, an aerosol, a fumigrant, a mosquito-coil and mosquito mat.

It is possible to blend the active ingredient of the present invention to a suitable other active ingredient such as the other insecticides, germicides, herbicides, plant growth regulators, and fertilizers in the preparation of the composition or in the application.

The present invention will be further illustrated by certain Reference examples, examples of Preparations, Compositions and Tests which are provided for purposes of illustration only and are not intended to be limiting the present invention.

REFERENCE EXAMPLE 1

Preparation of 5-fluoro-6-phenoxy picolinic aldehyde as the starting material

Dissolved in 160 ml of ethylalcohol were 45 g of 2-chloro-5-amino-6-phenoxypyridine (prepared by a known method as disclosed in West German Offenlegenschrift 2022024) and 130 g of $HPF_6$. While cooling this mixed solution at $-10°$ C., 28 g of butyl nitrite was added dropwise. After the reaction, the formed precipitate was collected by filtration, and washed with ethyl ether until the filtrate became colourless. The crystals thereby obtained were dried in vacuum at 50° C. for 8 hours to obtain 65 g of a product. This compound was transferred to a reaction flask, and gradually heated by means of a burner. Gradual decomposition with generation of a white smoke was observed. After the decomposition, an aqueous potassium carbonate solution was added for neutralization, and then 100 ml of chloroform was added for extraction to obtain a crude product.

The crude product was subjected to alumina column chromatography (developer: benzene) to remove coloured substances, and then distilled under reduced pressure to obtain 12.6 g of 2-chloro-5-fluoro-6-phenoxypyridine having a boiling point of 102° to 105° C./0.3 mmHg. The structure of this compound was confirmed by the nuclear magnetic resonance absorption spectra.

To a reaction flask(300 ml)equipped with a stirrer, a thermometer, a reflux condenser, a dropping funnel and a nitrogen supply tube, 1.45 g (0.06 gram-atom) of magnesium was introduced. Added thereto was 10 ml of dried tetrahydrofuran, and the air was replaced by nitrogen, and thereafter, nitrogen was continuously supplied from the nitrogen supply tube. Dissolved in tetrahydrofuran was 11.2 g (0.05 mole) of 2-chloro-5-fluoro-6-phenoxypyridine to obtain 100 ml of a solution, and a 1/10 amount (i.e. 10 ml) thereof was added to the reaction flask. The reaction flask was dipped in an oil bath to bring the temperature to from 35° to 40° C. After the initiation of the reaction, the remaining 9/10 amount (i.e. 90 ml) of the tetrahydrofuran solution was added dropwise while stirring to avoid a vigorous reaction. After the addition, the stirring was continued at 40° C. for further 30 minutes. Then, the reaction flask was immersed in an ice/water bath (0° C.) to cool it down, and then 4.4 g (0.06 moles) of dimethylformamide was added dropwise in 10 minutes. The mixture was stirred for 30 minutes at 40° C. After cooling, the tetrahydrofuran was distilled off under reduced pressure, and the residue was added to 10 ml of concentrated hydrochloric acid and 100 g of ice, thereby decomposing the remaining magnesium, and then neutralized with an aqueous solution of 1N sodium hydroxide to bring the pH to 7 to 8. The solution was transferred to a separating funnel, and after adding 100 ml of ethyl ether, it was adequately shaken. After washing the organic layer with a saturated aqueous sodium chloride solution and water, the organic layer was dried over anhydrous sodium sulfate, and the ethyl ether was distilled off under reduced pressure to obtain a crude product. This crude product was found to contain the desired 5-fluoro-6-phenoxy picolinic aldehyde (retention time 4.1 minutes) and the starting material 2-chloro-5-fluoro-6-phenoxypyridine in a proportion of 3:2, by the gas chromatography (Silicone DCHV 15%/Chromosorb WAW, 60 to 80 mesh, 1 m, the temperature rise from 150° C. at a rate of 20° C./min.).

Then, this crude product was purified by silica gel column chromatography (WAKO GEL Q-23 (trade name) which is available from Wako Chemical Corporation, 100 to 200 mesh, diameter of 4 cm × length of 42 cm, developer: benzene, an eluate of from 2000 ml to 2500 ml was collected), whereupon 3.1 g of the desired 5-fluoro-6-phenoxy picolinic aldehyde was obtained. The melting point was 66.0° to 71.0° C.

The structure of this product was confirmed by the nuclear magnetic resonance absorption spectra ($CDCl_3$, δ, ppm; 6.80 to 7.95 (7H, m), 9.64 (1H, s)) and the mass spectrography (m/z; 217 ($M^+$) and 188 ($M^+$—CHO)).

REFERENCE EXAMPLE 2

Preparation of cyano(5-fluoro-6-phenoxy-2-pyridyl) methyl alcohol as the starting material A mixture of 2.2 g of 5-fluoro-6-phenoxy picolinic aldehyde and 1.1 g of sodiumbisulfite was stirred vigorously in 10 ml of water until the mixture formed an emulsion. The resulting solution was extracted with 10 ml of ether. To the aqueous layer were added 0.54 g of sodium cyanide and 5 ml of water. After being stirred for 30 minutes, the reaction mixture was extracted with 20 ml of ether. The organic layer was dried over anhydrous sodium sulfate and concentrated to give 2.2 g of cyano(5-fluoro-6-phenoxy-2-pyridyl) methyl alcohol. The structure of this product was confirmed by the nuclear magnetic resonance absorption spectra ($CDCl_3$, δ, ppm; 4.20 (1H, bs), 5.34 (1H, s), 7.00–7,80 (7H, m)).

PREPARATION 1

Cyano(5-fluoro-6-phenoxy-2-pyridyl) methyl α-isopropyl-p-chlorophenyl acetate (Compound No. 1)

Into 20 ml of benzene, 2.4 g of cyano(5-fluoro-6-phenoxy-2-pyridyl) methyl alcohol and 0.8 g of pyridine were dissolved. The solution was stirred under cooling with ice and 2.3 g of α-isopropyl-p-chlorophenyl acetic acid chloride was added dropwise to the solution. After reacting them for 1 hour, the reaction product was washed twice with 10 ml of water and the organic layer was dried over anhydrous sodium sulfate and benzene was distilled off under a reduced pressure. The residual oily product was purified by a column chromatography (alumina; developing solvent: benzene)to obtain 4.1 g of the object compound. $n_D^{20}$ 1.5464. NMR spectrum: δ, ppm, $CDCl_3$;

0.70 (3H, d, J=6.0 Hz), 0.90 (1.5H, d, J=6.0 Hz) 0.98 (1.5H, d, J=6.0 Hz), 2.30 (1H, m), 3.18 (0.5H, d, J=10.0 Hz), 3.20 (0.5H, d, J=10.0 Hz), 6.17 (1H, bs), 6.95–7.65 (11H, m)

PREPARATION 2

Cyano(5-fluoro-6-phenoxy-2-pyridyl) methyl trans-2,2-dimethyl-3-(p-t-butylphenyl)cyclopropanecarboxylate (Compound No. 4)

Into 20 ml of n-hexane, 2.2 g of 5-fluoro-6-phenoxy picolinic aldehyde, 2.7 g of trans-2,2-dimethyl-3-(p-tert-butylphenyl)cyclopropanecarboxylic acid chloride, 0.6 g of sodium cyanide, 1 ml of water and 0.1 g of tetra-n-butylammonium chloride were added.

The mixture was vigorously stirred at room temperature to react them for 30 hours. After the reaction, the organic layer was washed with 10 ml of water and dried over anhydrous sodium sulfate and n-hexane was distilled off under a reduced pressure. The residual crude product was purified by a column chromatography (alumina; developing solvent: benzene) to obtain 3.8 g of the object compound. $n_D^{20}$ 1.5430.

NMR spectrum: δ, ppm, $CDCl_3$; 0.98 (3H, bs), 1.28 (1.5H, s), 1.30 (9H, s), 1.39 (1.5H, s), 2.05 (1H, m), 2.70 (1H, m), 6.30 (1H, m), 6.90–7.70 (m, 11H)

PREPARATION 3

Cyano(5-fluoro-6-phenoxy-2-pyridyl) methyl (1R, cis)-2,2-dimethyl-3-(2,2-dibromovinyl)cyclopropane carboxylate (Compound No. 6)

Into 20 ml of hexane, 3.2 g of acid chloride (prepared from (1R, cis)-2,2-dimethyl-3-(2,2-dibromovinyl)cyclopropane carboxylic acid ($[\alpha]_D^{20}+26.3$ (C=0.81, $C_6H_6$)) and thionyl chloride), 2.2 g of 5-fluoro-6-phenoxy picolinic aldehyde, 0.6 g of sodium cyanide, 1 ml of water and 0.1 g of tetrabutylammonium chloride were added. The mixture was vigorously stirred at room temperature to react them for 24 hours. After the reaction, 50 ml of ethyl ether and 20 ml of water were added. The organic layer was washed with 10 ml of water and dried over anhydrous sodium sulfate and n-hexane was distilled off to obtain a crude ester. The crude ester was purified by a column chromatography (alumina; developing solvent: benzene) to obtain 4.5 g of the object compound. $n_D^{20}$ 1.5816.

$[\alpha]_D^{20}+7.85$ (C=0.48, $C_6H_6$) and $[\alpha]_D^{20}+9.52$ (C=0.52, $CHCl_3$).

NMR spectrum: δ, ppm, $CDCl_3$; 1.25 (6H, bs), 2.10 (2H, m), 6.24 (1H, s), 6.66 (1H, d, J=7.0 Hz), 6.80–7.75 (7H, m).

Certain examples of the compositions of the compounds of the present invention as insecticides are provided for purposes of illustration only and are not intended to be limiting the present invention.

| Composition 1 Emulsifiable concentrate: | |
|---|---|
| Active ingredient | |
| Compound No. 1: | 10 wt. parts |
| Xylene: | 80 wt. parts |
| Sorpol 2680 (Toho Chem.): | 10 wt. parts |

The components were uniformly mixed to prepare an emulsifiable concentrate. The emulsifiable concentrate was diluted with water to 50–100,000 times and it was sprayed in amounts of 10–500 liter/10 ares.

As the active ingredient, other compounds in Table 1 were also used.

| Composition 2 Oil solution: | |
|---|---|
| Active ingredient | |
| Compound No. 1: | 50 wt. parts |
| Methyl cellosolve: | 50 wt. parts |

The components were uniformly mixed to obtain an oily solution.

The oil solution was applied in amounts of 0.1 to 50 $ml/m^2$ to a drain or puddle or in amounts of 10–100 ml/10 ares by airplain spray. As the active ingredient, other compounds in Table 1 were also used.

| Composition 3 Wettable powder: | |
|---|---|
| Active ingredient | |
| Compound No. 4: | 25 wt. parts |
| Zeeklite PFP: | 65 wt. parts |
| Carplex #80: | 2 wt. parts |
| Sorpol 5050: | 2 wt. parts |
| Sodium ligninesulfonate: | 6 wt. parts |

The components were uniformly ground and mixed to obtain a wettable powder. The wettable powder was diluted with 100 to 250,000 times of water and it was sprayed in amounts of 20 to 500 liter/10 ares.

As the active ingredient, other compounds in Table 1 were also used.

| Composition 4 Dust: | |
|---|---|
| Active ingredient | |
| Compound No. 6: | 3.0 wt. parts |
| Carplex #80: | 0.5 wt. parts |
| Clay: | 95 wt. parts |
| Diisopropyl phosphate: | 1.5 wt. parts |

The components were uniformly mixed to obtain a dust. The dust was applied in amounts of 0.03 to 15 kg/10 ares.

As the active ingredient, other compounds in Table 1 were also used.

The insecticidal activities of the compounds of the present invention are illustrated by the following tests.

As references, the following active ingredients were used.

Reference compound A

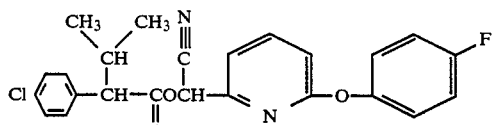

(Japanese Patent Application No. 111460/1979)

Reference compound B

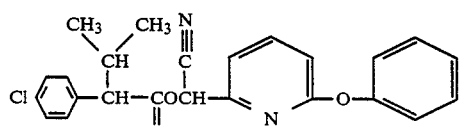

(Japanese Unexamined Patent Publication No. 115869/1979)

Reference compound C

-continued (Japanese Patent Application No. 140513/1979)

Reference compound D (Japanese Patent Application No. 140513/1979)

Reference compound E (Japanese Patent Application No. 116589/1979)

Reference compound F (Japanese Unexamined Patent Publication No. 79368/1979)

Reference compound G (Japanese Patent Application No. 116589/1979)

Reference compound H (Japanese Unexamined Patent Publication No. 79368/1979)

Reference compound I (Japanese Unexamined Patent Publication No. 112881/1979)

EXPERIMENT 1

Contact test for killing green rice leafhopper

Stems and leaves of a rice seedling were dipped in each emulsion of each active ingredient of the present invention or a reference compound for 10 seconds and were dried in air. The stems and leaves were covered with a glass cylinder. Adult green rice leafhoppers which are resistant to the conventional organic phosphorus type insecticide were released into the glass cylinder which was covered with a cover having holes and was maintained in a constant temperature room at 25° C. for 48 hours and each percent mortality was determined and median lethal dose ($LC_{50}$) was calculated in Finny's graphic method.

The results are shown in Table 2.

TABLE 2

| Active ingredient | $LC_{50}$ (ppm) |
|---|---|
| Compound No. 1 | 0.26 |
| Reference Compd. A | 1.4 |
| Reference Compd. B | 5.0 |
| Compound No. 2 | 0.28 |
| Reference Compd. C | 76.0 |
| Reference Compd. D | 6.0 |
| Compound No. 3 | 0.7 |
| Reference Compd. E | 6.0 |
| Compound No. 4 | 1.3 |
| Reference Compd. G | 32.0 |
| Reference Compd. H | 6.4 |
| Compound No. 5 | 0.40 |
| Compound No. 6 | 0.31 |
| Reference Compd. I | 3.7 |

EXPERIMENT 2

Contact test for killing Common cutworm

Leaves of cabbage were dipped in each aqueous emulsion of each active ingredient of the compounds of the invention or the reference for 10 seconds. The leaves were taken up and dried in air and put in a Petri dish. Common cutworms (second instar) were put in the Petri dish which was covered with a cover having many holes. The Petri dish was maintained in a constant temperature room at 25° C. for 48 hours and each percent mortality was determined and median lethal dose ($LC_{50}$) was calculated in Finny's graphic method.

The results are shown in Table 3.

TABLE 3

| Active ingredient | $LC_{50}$ (ppm) |
|---|---|
| Compound No. 1 | 0.43 |
| Reference Compd. A | 3.1 |
| Reference Compd. B | 1.7 |
| Compound No. 2 | 3.0 |
| Reference Compd. C | 5.0 |
| Reference Compd. D | 9.0 |
| Compound No. 3 | 1.3 |
| Reference Compd. E | 13.0 |
| Reference Compd. F | 15.0 |
| Compound No. 4 | 4.0 |
| Reference Compd. G | 12.0 |
| Compound No. 5 | 0.31 |
| Compound No. 6 | 0.24 |
| Reference Compd. I | 0.0 |

EXPERIMENT 3

Test for killing Green peach aphid

Each emulsifiable concentrate of the compound of the present invention or the reference compound was diluted with water to a predetermined concentration. Green peach aphid were inoculated on leaves in a Petri dish having a diameter of 3 cm and 2 ml of each emulsion was sprayed and it was covered. The Petri dish was maintained in a constant temperature room at 25° C. for 48 hours and each percent of mortality was determined and median lethal dose ($LC_{50}$) was calculated in Finny's graphic method.

The results are shown in Table 4.

TABLE 4

| Active ingredient | LC$_{50}$ (ppm) |
|---|---|
| Compound No. 2 | 2.3 |
| Reference Compd. D | 26.0 |
| Compound No. 4 | 4.6 |
| Reference Compd. H | 12.0 |
| Compound No. 5 | 1.84 |
| Reference Compd. I | 34.0 |

EXPERIMENT 4

Test for killing Kanzawa spider mite

Leaves of kidney bean was cut by a leaf-punch in a form of circle having a diameter of 1.5 cm. The leaf-discs were put on a wet filter paper on a polystyrene cup having a diameter of 7 cm. Ten of Kanzawa spider mites were inoculated on the leaf-discs in the cup. Half days after the inoculation, each solution prepared by diluting each emulsifiable concentrate of the present invention or each reference compound with a spreader (Nitten S 4,000 times manufactured by Nissan Chem.) at each predetermined concentration was sprayed by a rotary spray for 2 ml. per each cup.

Numbers of mortalities of mites were measured after 48 hours from the spraying and percent mortaliteis were calculated and median lethal dose (LC$_{50}$) was calculated in Finny's graphic method.

The results are shown in Table 5.

TABLE 5

| Active ingredient | LC$_{50}$ (ppm) |
|---|---|
| Compound No. 1 | 6.3 |
| Reference Compd. A | 100 |
| Compound No. 2 | 12 |
| Reference Compd. C | >100 |
| Compound No. 4 | 0.32 |
| Reference Compd. G | 2.0 |
| Compound No. 5 | 5.4 |
| Reference Compd. I | >100 |

EXPERIMENT 5

Contact test for killing Twenty-eight-spotted Ladybeetle

Leaves of tomato were dipped in each emulsion of each active ingredient of the present invention or the reference for 10 seconds. The leaves were taken up and dired in air and put in a Petri dish. Ten of Twenty-eight-spotted Ladybeetles (second instar) were put in the Petri dish which was covered with a cover. The Petri dish was maintained in a constant temperature room at 25° C. for 48 hours and percent mortality was determined and median lethal dose (LC$_{50}$) was calculated in Finny's graphic method.

The results are shown in Table 6.

TABLE 6

| Active ingredient | LC$_{50}$ (ppm) |
|---|---|
| Compound No. 1 | 0.05 |
| Compound No. 2 | 0.5 |
| Reference Compd. C | 21.0 |
| Reference Compd. D | 0.9 |
| Compound No. 3 | 0.26 |
| Reference Compd. F | 2.0 |
| Compound No. 5 | 0.03 |
| Compound No. 6 | 0.02 |

We claim:

1. Fluorine substituted pyridine methyl esters having the formula

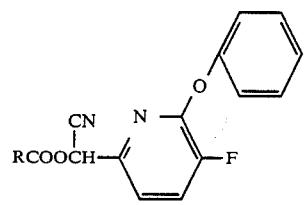

wherein R represents

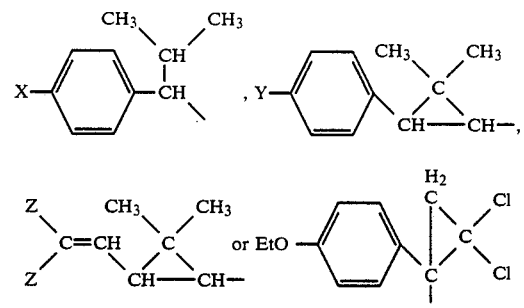

in which X is chlorine or difluoromethoxy; Y is chlorine or tert-butyl; and Z is a halogen atom.

2. Cyano(5-fluoro-6-phenoxy-2-pyridyl) methyl α-isopropyl-p-chlorophenyl acetate according to claim 1.

3. Cyano(5-fluoro-6-phenoxy-2-pyridyl) methyl α-isopropyl-p-difluoromethyoxyphenyl acetate according to claim 1.

4. Cyano(5-fluoro-6-phenoxy-2-pyridyl) methyl 2,2-dimethyl-3-(p-chlorophenyl) cyclopropanecarboxylate according to claim 1.

5. Cyano(5-fluoro-6-phenoxy-2-pyridyl) methyl 2,2-dimethyl-3-(p-tert-butylphenyl) cyclopropanecarboxylate according to claim 1.

6. Cyano(5-fluoro-6-phenoxy-2-pyridyl) methyl 2,2-dimethyl-3-(2,2-dichlorovinyl) cyclopropanecarboxylate according to claim 1.

7. Cyano(5-fluoro-6-phenoxy-2-pyridyl) methyl 2,2-dimethyl-3-(2,2-dibromovinyl) cyclopropanecarboxylate according to claim 1.

8. Cyano(5-fluoro-6-phenoxy-2-pyridyl) methyl 2,2-dichloro-1-(p-ethoxyphenyl) cyclopropanecarboxylate according to claim 1.

9. An insecticidal and acaricidal composition which comprises an effective amount of an insecticidal and acaricidal compound of fluorine substituted pyridine methyl ester having the formula (I)

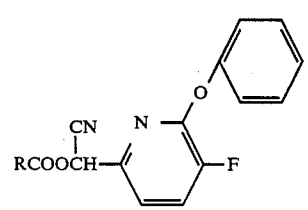

wherein R represents

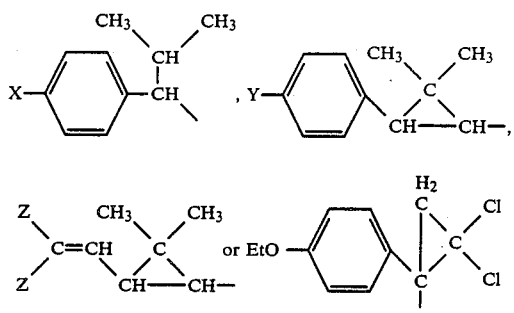

in which X is chlorine or difluoromethoxy; Y is chlorine or tert-butyl; and Z is a halogen atom and an adjuvant in a form of a solution, a dispersion, an emulsifiable concentrate, an oil solution, a wettable powder, a dust, a granule, a tablet, a pellet, a paste, an areosol, a smudge, a mosquito-repellent incense.

10. The insecticidal and acaricidal composition according to claim 9 which further comprises a synergist of piperonyl butoxide, octachlorodipropyl ether or N-octyl bicycloheptane dicarboxyimide.

11. The insecticidal and acaricidal composition according to claim 9 which comprises said insecticidal and acaricidal compound in an amount in the range of 0.01 to 10,000 ppm.